United States Patent [19]

Witiak et al.

[11] Patent Number: 4,529,773
[45] Date of Patent: Jul. 16, 1985

[54] ALKALI-SOLUBLE EMULSION POLYMERS IN ACIDIC SURFACTANT COMPOSITIONS

[76] Inventors: David Witiak, 500 Stony Hill Rd., Yardley, Pa. 19067; Jean Dupré, 45 Snowball Dr., Levittown, Pa. 19056

[21] Appl. No.: 358,993

[22] Filed: Mar. 17, 1982

[51] Int. Cl.$^3$ .............................................. C08L 33/02
[52] U.S. Cl. .................................................... 524/558
[58] Field of Search ........................................ 524/558

[56] References Cited

U.S. PATENT DOCUMENTS

| | | | |
|---|---|---|---|
| 3,652,497 | 3/1972 | Junar | 526/317 |
| 3,657,175 | 4/1972 | Zimmerman | 524/558 |
| 3,779,970 | 12/1973 | Evani | 260/29.6 |
| 3,891,591 | 6/1975 | Chang | 260/29.6 |
| 3,894,980 | 7/1975 | DeTommaso | 524/558 |
| 3,960,935 | 6/1976 | Samour | 526/304 |
| 4,138,381 | 2/1979 | Chang | 526/317 |
| 4,230,844 | 10/1980 | Chang | 525/375 |
| 4,268,641 | 5/1981 | Koenig | 524/558 |
| 4,338,239 | 7/1982 | Dammann | 524/558 |

OTHER PUBLICATIONS

European Patent Application 0013836, published 6/8/80.

Primary Examiner—Paul R. Michl

[57] ABSTRACT

Alkali-soluble emulsion polymers that have been activated by neutralization to a pH above 6.5, and subsequently acidified in the presence of a surfactant, are useful as thickeners in acidified, surfactant-containing compositions.

7 Claims, No Drawings

ALKALI-SOLUBLE EMULSION POLYMERS IN ACIDIC SURFACTANT COMPOSITIONS

BACKGROUND OF THE INVENTION

This invention relates to thickened aqueous solutions, and more particularly to a method of thickening low-pH, aqueous, surfactant-containing compositions, and the compositions so thickened.

It is desirable, for various reasons, to thicken, or increase the viscosity of, aqueous solutions. Additives for thickening are widely known, and include nonionic thickeners, exemplified by natural gums such as guar and locust bean extract, starches and cellulose and their derivatives, such as hydroxyalkyl celluloses and carboxyalkyl celluloses. They also include ionic thickeners, exemplified by certain polyelectrolyte resins such as polymers of acrylic acid and methacrylic acid, and copolymers containing hydrophobic groups based upon long, fatty-acid constituents and hydrophilic linkages based upon poly(oxyethylene) chains.

The nonionic thickeners are relatively insensitive to pH, but they are also relatively expensive, require special processing techniques for incorporation into aqueous compositions, must be used in comparatively high concentration, and tend to exhibit viscosity loss on storage as a result of hydrolysis. The ionic thickeners are therefore of greater interest, since they overcome many of these deficiencies. Especially of interest are the alkali-soluble emulsion polymer thickeners which are supplied as acidic emulsions of relatively low viscosity, and are neutralized at least partially to the salt form either prior to, simultaneously with, or subsequent to incorporation into the aqueous compositions. The neutralization is accompanied by dissolution of the thickener emulsion, and by a marked increase in the thickener viscosity. Especially in the case of detergents and other surfactant-based compositions, the composition itself is neutral or alkaline, so this neutralization of the thickener emulsion presents no problem.

A need exists, however, for thickening acidic surfactant compositions. While by no means the only such acidic surfactant compositions, examples of these are the "natural-pH" shampoo compositions, having a pH from about 5.5 to about 6.5, a range said to include the pH of healthy human hair and scalp. As the alkali-soluble emulsion polymer thickeners are insoluble in acidic solutions, and only develop high viscosities upon neutralization to a pH above 6.5–7.0, they are not used in the acidic surfactant compositions. Rather, the nonionic thickeners are used because of their stability at low pH, despite the above-listed disadvantages.

SUMMARY OF THE INVENTION

We have discovered acidic compositions containing alkali-soluble emulsion polymer thickeners and surfactants which are surprisingly viscous in view of the known viscosity decrease with decreasing pH of such thickeners, and we have discovered a process by which surfactant compositions having a pH below about 7.0, and preferably between about 1.2 and about 7.0 may be thickened effectively. The process of the present invention comprises the steps, performed in any order, of (a) mixing the alkali-soluble emulsion polymer thickener with an aqueous surfactant-containing solution, and (b) neutralizing the thickener, and the step, performed subsequent to the two above steps, of (c) adjusting the pH of the mixture to 7.0 or below, preferably between 7.0 and 1.2, and more preferably between 5.0 and 6.5.

DETAILED DESCRIPTION

The thickeners of the present invention are alkali-soluble emulsion polymer thickeners, materials which, as produced, are non-water-soluble emulsions, but which dissolve and show a marked increase in viscosity on addition of alkali. Among these alkali-soluble emulsion polymer thickeners, the preferred thickeners are those described in U.S. patent application Ser. No. 101,615, filed Dec. 10, 1979, which is hereby incorporated herein by reference. While the preferred thickeners themselves and the method of preparing them are set forth in detail in that application, they are also briefly set forth below. The thickeners are aqueous dispersions of water-insoluble, emulsion copolymers obtained by aqueous emulsion copolymerization of the three following monomers, and optionally the fourth monomer, set forth below:

(1) Methacrylic acid or acrylic acid, (2) An acrylic or methacrylic acid ester of a $C_8$–$C_{30}$ alkyl, alkylaryl or polycyclic hydrocarbyl monoether of a polyethylene glycol having at least two oxyethylene units, preferably having 10 to 40 oxyethylene units, and having as many as 70 or so oxyethylene units, this ester being defined by the following general formula:

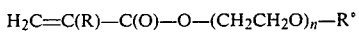

$$H_2C=C(R)-C(O)-O-(CH_2CH_2O)_n-R°$$

wherein

R is H or $CH_3$, the latter being preferred, n is at least 2, and preferably has an average value of at least 10, up to 40 to 60 or even up to 70 or so, and R° is a hydrophobic group, for example an alkyl, alkylaryl, or polycyclic alkyl group having 8 to 30 carbon atoms, preferably 16 to 18 carbon atoms, or having an average of 12 to 18 or more carbon atoms, (3) A $C_1$–$C_4$ alkyl acrylate or methacrylate, preferably ethyl acrylate, butyl acrylate or methyl methacrylate, and (4) Optionally, a small amount of a polyethylenically unsaturated monomer.

In general, the emulsion copolymer dispersions obtained have solids contents from 25 to 50% by weight, and the 3-component copolymer dispersion has a weight-average molecular weight of about 100,000 to several million. The chain-transfer agent may be used to obtain molecular weights in the lower part of the range, or even down to about 80,000. Alternatively, use of 0.05% to about 1.0% of monomer component (4), based on total monomers, serves to provide molecular weights in or above the higher portion of the range mentioned.

The relative proportions of the first three components fall in the broad range of (1) 20–50 weight percent, (2) 0.5 to 25 weight percent, and (3) at least 30 weight percent, the total percentages of the three components being 100. The preferred ranges are (1) 35–45%, (2) 1–15% and (3) 40–60%. In component (2), R° may be octyl ($C_8$), lauryl ($C_{12}$), tridecyl ($C_{13}$), myristyl ($C_{14}$), or pentadecyl ($C_{15}$), but preferably $C_{12}$ to $C_{18}$ or mixtures thereof, examples being lauryl, cetyl, palmityl, and stearyl. R° may be alkylaryl, such as octyl and vinylphenyl, or polycyclic alkyl such as cholesterol and lanosterol. A mixture of several $C_8$–$C_{30}$ alkyl ethers may be used. These emulsion copolymers may be produced by conventional aqueous emulsion polymerization techniques, using appropriate emulsifiers for emulsifying the monomer and for maintaining the polymer obtained in a stable-dispersed condition. Additional information on the emulsion polymerization may be found in the above-referenced application.

The amount of thickener to be used in the composition depends largely upon the degree of thickening desired. While high concentrations, as for instance, above 10% by weight of thickener, are operable, the viscosities obtained would be extremely high, and would therefore be expected to be both physically impractical and uneconomical. The preferred maximum level of thickener is therefore below 5%, and more preferably below 2.5%, by weight. The minimum level depends again primarily upon the degree of thickening desired, and it is expected that a measurable viscosity increase will occur at thickener levels as low as 0.05%.

As mentioned above, the thickeners of the present invention are water-insoluble, alkali-soluble emulsions having a milky appearance. Upon addition of a neutralizing agent, as for example an alkali metal hydroxide, ammonium hydroxide, soda ash or triethanolamine, the emulsion dissolves to form an essentially clear solution and the viscosity increases sharply. Upon reacidification, most aqueous thickener solutions will coagulate and revert to low-viscosity suspensions. We have discovered, however, that in the presence of from about 5 to about 40 weight percent, and more preferably from about 10 to about 25 weight percent, of surfactant, if the solution is first neutralized to a pH above 6.5 and preferably above 7.0, and subsequently is acidified to a pH below 7.0, preferably between 7.0 and about 1.2, more preferably between 7.0 and about 3.5, and still more preferably between about 5.0 and 6.5, then the coagulation does not occur, and while some of the viscosity of the neutralized thickener is lost, the acidified composition is thickened, that is, it retains a significantly higher viscosity than that of the equivalent mixture, which is acidified without first being neutralized as described. Although no theoretical explanation is suggested herein for the phenomenon described above, the thickener solution neutralized as described above shall be referred to herein as "activated". As the thickening property of the activated thickener is lost upon acidification in the absence of a surfactant, an activated thickener acidified in the absence of a surfactant shall be considered to have lost its activation, while an activated thickener which is acidified in the presence of a surfactant as described below, and which retains a significant amount of its thickening power, shall continue to be considered an activated thickener.

It should be noted that some activation may occur in thickener-surfactant mixtures there are not neutralized to a pH above 6.5. In general, this activation develops more slowly, and to a lesser extent, than when neutralization is to the preferred pH levels.

The surfactants useful in the present invention generally include those anionic, nonionic and amphoteric surfactants which are compatible with the thickener used, that is, which cause no precipitation of the thickener in the solution. Common surfactants may be used, including but not limited to, sodium, ammonium and amine salts of fatty alcohol sulfates and fatty alcohol ether sulfates, alkanol ethoxylates, alkyl phenyl ethoxylates, alkanolamides, and alpha olefin sulfonates. The surfactant level required in the present invention is at least about 5% by weight, and more preferably at least about 10% by weight. The maximum surfactant level depends upon the desired physical properties; surfactant solutions containing up to about 40% by weight of surfactant are operable, but are usually viscous enough that additional thickening is not required. At surfactant concentrations greater than 40% the solution viscosity is so great as to cause processing difficulty. More preferably the maximum concentration of surfactant is about 25% by weight. All surfactant concentrations are on a surfactant solids basis as a weight percentage of the total mixture.

The above-referenced U.S. patent application, Ser. No. 101,615, discloses a phenomenon termed "surfactant co-thickening", by which a synergistic enhancement of thickening occurs when the thickener is combined with small amounts of surfactant. Although the exact mechanism is unknown by which the effects observed in the present invention occur, it is presumed to be different from the "surfactant co-thickening" phenomenon, as the optimum surfactant levels of the present invention are significantly higher than those for "surfactant co-thickening".

It is critical to the process of the present invention that the thickener, which contains free acid groups as it is prepared, be at least partially neutralized to the salt form prior to acidification of the mixture; it is further critical that the neutralized thickener be in the presence of the surfactant at the time the acidification occurs. While inadequately neutralized thickener is operable in the present invention, it is wasteful, because failure to adequately neutralize the thickener results in a reduced contribution of the unneutralized thickener to the mixture viscosity. Similarly, an excess of the neutralizing agent is undesirable, as it must react with the acidifying agent before the mixture pH can be adjusted to the desired, acidic level. The preferred amount of neutralizing agent is that amount required to adjust the mixture pH to above 6.5, and more preferably to between 7.0 and 7.5. This corresponds approximately to 0.5–0.8 equivalent of neutralizing agent per equivalent of acid groups in the thickener. The mixture may be acidified with any acid that is capable of reducing the pH to the desired level. The selection of the specific acid will ordinarily depend upon factors not related to the present invention. For example, in shampoo and cosmetic applications, low toxicity may be an important factor in acid selection, and citric acid is preferred in many such applications. Because the mixture contains a high concentration of organic components, the use of oxidizing acids for acidification is not preferred.

In simple solutions of surfactants, water and thickeners the desired viscosity increase at low pH occurs, but is sometimes accompanied by turbidity. To produce a clear, totally compatible solution, that is, one free from turbidity or other evidence of partial precipitation or other incompatibility, it is sometimes necessary to add a stabilizer. Materials which have been found effective as stabilizers in the mixtures of the present invention include the class of materials generally referred to as foam stabilizers. These include fatty acid alkanolamides, especially those in which the carboxyl group is substituted by a long-chain, preferably $C_{12}$–$C_{22}$, alkane, such as lauric diethanolamide, coconut acid diethanolamide and the like. These foam stabilizers are preferably present in the mixture at a level from about 0.5% to about 5% by weight, the exact amount being selected as that which prevents turbidity in the thickened, acidified solution.

EXAMPLES

The following examples are intended to illustrate the present invention, but not to limit it except as it is limited in the claims. All percentages are by weight, unless otherwise specified, and all reagents used are of good commercial grade.

The thickened surfactant mixtures of the following examples were prepared according to the following procedure:

The alkali-soluble emulsion is dispersed in deionized water. The major surfactant component is added and mixed, the alkanolamide is added, and finally the neutralizing agent, which is 0.5 equivalents of sodium hydroxide per equivalent of thickener carboxyl groups as a 10% aqueous solution, is added. The solution is mixed by stirring for about 15 minutes, and is allowed to stand overnight before the viscosity is measured. To obtain the acidified solution, varying amounts of a 20% aqueous solution of citric acid is added to 50-g aliquots of the thickened surfactant solution until the desired pH is obtained.

Viscosities given in the following examples were obtained using a Brookfield Model LVT Viscometer at the indicated spindle speed. It should be noted that the thickened solutions are pseudoplastic, or shear thinning, so that shear rate, as indicated herein by spindle speed, is an important parameter in viscosity measurement.

EXAMPLE 1

Mixtures were prepared containing an anionic surfactant at varying levels and an alkali-soluble, ionic thickener of the present invention at a constant level, and viscosities of the mixtures were determined at various pH levels to establish the criticality of surfactant to the preservation of viscosity at low pH levels. The surfactant used was sodium lauryl sulfate, and the thickener was as described in the specification above, wherein component (1) is methacrylic acid (40%), component (2) is as represented by the general formula wherein R is $CH_3$, n is 20 and $R°$ is a mixture of $C_{16}$ and $C_{18}$ alkyls (10%), component (3) is ethyl acrylate (50%) and component (4) is not used. The mixture is neutralized with 0.8 equivalents of sodium hydroxide, and the neutralized mixture was acidified with citric acid. Mixtures containing 1.0% of the thickener and the indicated amount of sodium lauryl sulfate were prepared according to the above procedure, and acidified to the indicated pH. The viscosity at a spindle speed of 12 rpm was determined, and the results are given in Table I.

TABLE 1

| Surfactant Concentration | pH | Viscosity Centipoises |
|---|---|---|
| 0 | 7.0 | $2.3 \times 10^4$ |
| 0 | 6.2 | $5.0 \times 10^3$ |
| 0 | 5.9 | $6.0 \times 10^{0(t)}$ |
| 1.0 | 7.4 | $4.0 \times 10^4$ |
| 1.0 | 6.7 | $2.3 \times 10^{3(t)}$ |
| 1.0 | 6.2 | $2.2 \times 10^{1(t)}$ |
| 1.0 | 5.2 | $4.0 \times 10^{0(t)}$ |
| 5.0 | 7.5 | $7.2 \times 10^3$ |
| 5.0 | 6.9 | $1.6 \times 10^2$ |
| 5.0 | 6.6 | $5.2 \times 10^{1(t)}$ |
| 5.0 | 5.4 | $2.6 \times 10^{1(t)}$ |
| 5.0 | 4.9 | $2.7 \times 10^{1(t)}$ |
| 10.0 | 7.9 | $1.0 \times 10^3$ |
| 10.0 | 7.0 | $1.8 \times 10^2$ |
| 10.0 | 6.7 | $5.4 \times 10^{1(t)}$ |
| 10.0 | 5.7 | $4.6 \times 10^{1(t)}$ |
| 10.0 | 5.3 | $4.4 \times 10^{1(t)}$ |
| 10.0 | 4.6 | $5.0 \times 10^{1(t)}$ |
| 15.0 | 8.3 | $3.3 \times 10^2$ |
| 15.0 | 2.2 | $1.7 \times 10^2$ |
| 15.0 | 6.9 | $1.0 \times 10^2$ |
| 15.0 | 6.1 | $7.0 \times 10^{1(t)}$ |
| 15.0 | 5.4 | $1.2 \times 10^{2(t)}$ |
| 15.0 | 4.5 | $1.4 \times 10^{2(t)}$ |
| 20.0 | 8.2 | $3.7 \times 10^2$ |
| 20.0 | 7.3 | $3.3 \times 10^2$ |
| 20.0 | 6.3 | $1.3 \times 10^2$ |
| 20.0 | 5.8 | $2.5 \times 10^{2(t)}$ |
| 20.0 | 5.4 | $2.8 \times 10^{2(t)}$ |
| 20.0 | 4.8 | $3.0 \times 10^{2(t)}$ |
| $15.0^1$ | 9.0 | $3.5 \times 10^0$ |
| $15.0^1$ | 7.1 | $3.1 \times 10^0$ |
| $15.0^1$ | 6.0 | $2.8 \times 10^0$ |
| $15.0^1$ | 5.2 | $3.0 \times 10^0$ |
| $15.0^1$ | 4.5 | $3.1 \times 10^0$ |

$^1$15% solution of sodium lauryl sulfate, without thickener
$^{(t)}$Turbid mixture.

It is readily apparent from the data presented in Table I that the surfactant solution without thickeners is almost insensitive to pH and possesses very low viscosity, that the thickened solutions containing less than 5% surfactant are extremely sensitive to pH, losing all practical thickening as the solution becomes acid, and that as the surfactant level increases the pH sensitivity of the thickened solution decreases and the viscosity of the acidic solution rises significantly.

EXAMPLE 2

Mixtures containing various surfactants at a constant level, with a constant level of foam stabilizers, were prepared both with and without thickener, to demonstrate the effectiveness of the thickener at various pH levels. The mixtures were prepared according to the procedure given above, and various pH levels of the mixtures were measured for viscosity at a spindle speed of 12 rpm. The composition of the mixtures is given in Table II, and the results are given in Table III.

TABLE II

| Mixture A: | 17% sodium lauryl ether sulfate; 3% lauric diethanolamide; 1.5% thickener of Example 1; 0.5 equivalents sodium hydroxide; acidified with citric acid. |
|---|---|
| Mixture B: | As Mixture A, but thickener omitted. |
| Mixture C: | 17% sodium lauryl sulfate; 3% lauric diethanolamide; 1.0% thickener of Example 1; 0.5 equivalents sodium hydroxide; acidified with citric acid. |
| Mixture D: | As Mixture C, but thickener omitted. |
| Mixture E: | 17% Tween-20 (polysorbate-20 ethylene oxide groups, product of ICI Americas); 3% coconut fatty acid diethanolamide; 1% Miranol C2MSF (amphoteric surfactant, product of Miranol Chemical Co., Inc.); 2% thickener of Example 1; 0.5 equivalents sodium hydroxide; acidified with citric acid. |
| Mixture F: | 17% triethanolamine lauryl sulfate; 3% coconut fatty acid diethanolamide; 1% Miranol C2MSF (amphoteric surfactant, product of Miranol Chemical Co., Inc.); 2% thickener of Example 1, 0.5 equivalents sodium hydroxide; acidified with citric acid. |
| Mixture G: | As Mixture F, but thickener omitted. |
| Mixture H: | 17% Siponate A-246LX (sodium salt of $C_{14}$-$C_{16}$ alpha olefin sulfonate, product of Alcolac Inc.); 3% coconut fatty acid diethanolamide; 1.5% thickener of Example 1; 0.5 equivalents sodium |

TABLE II-continued

| | |
|---|---|
| | hydroxide; acidified with citric acid. |
| Mixture I: | As Mixture H, but thickener omitted. |
| Mixture J: | 17% sodium lauryl sulfate; 3% lauric diethanolamide; 1.5% thickener of Example 1; 0.5 equivalents of sodium hydroxide; acidified with citric acid. |
| Mixture K: | 17% sodium lauryl sulfate; 3% lauric diethanolamide; 1.5% thickener of Example 1; 0.5 equivalents of sodium hydroxide; acidified with hydrochloric acid. |
| Mixture L: | 17% sodium lauryl sulfate; 3% lauric diethanolamide; 1.5% copolymer of 65% methacrylic acid, 35% ethyl acrylate; 0.5 equivalents sodium hydroxide; acidified with citric acid. |
| Mixture M: | 17% sodium lauryl sulfate; 3% lauric diethanolamide; 15% copolymer of 40% methacrylic acid, 60% ethyl acrylate; 0.5 equivalents sodium hydroxide; acidified with citric acid. |
| Mixture N: | 17% Siponate A-246LX (sodium salt of $C_{14}$-$C_{16}$ alpha olefin sulfonate, product of Alcolac Inc.); 3% coconut fatty acid diethanolamide; 2.0% copolymer of 65% methacrylic acid, 35% ethyl acrylate; 0.5 equivalents sodium hydroxide; acidified with citric acid. |
| Mixture O: | 17% Siponate A-246LX (sodium salt of $C_{14}$-$C_{16}$ alpha olefin sulfonate, product of Alcolac Inc.); 3% coconut fatty acid diethanolamide; 2.0% copolymer of 40% methacrylic acid, 60% ethyl acrylate; 0.5 equivalents sodium hydroxide; acidified with citric acid. |

TABLE III

| Mixture | pH | Viscosity Centipoises |
|---|---|---|
| A | 7.8 | $2.8 \times 10^4$ |
| | 6.1 | $3.6 \times 10^3$ |
| | 5.9 | $3.8 \times 10^3$ |
| | 5.6 | $4.8 \times 10^3$ |
| | 4.8 | $5.8 \times 10^3$ |
| | 4.4 | $5.5 \times 10^3$ |
| B | 7.2 | $5.0 \times 10^1$ |
| | 4.7 | $8.4 \times 10^1$ |
| | 4.5 | $8.5 \times 10^1$ |
| | 4.3 | $7.0 \times 10^1$ |
| | 4.0 | $6.7 \times 10^1$ |
| | 3.9 | $5.6 \times 10^1$ |
| C | 8.1 | $9.2 \times 10^3$ |
| | 7.1 | $8.1 \times 10^3$ |
| | 6.2 | $1.6 \times 10^3$ |
| | 5.3 | $2.0 \times 10^3$ |
| | 4.6 | $3.0 \times 10^3$ |
| D | 6.7 | $2.8 \times 10^1$ |
| | 5.9 | $3.0 \times 10^1$ |
| | 4.9 | $3.0 \times 10^1$ |
| | 3.9 | $2.5 \times 10^1$ |
| | 3.2 | $1.5 \times 10^1$ |
| E | 7.0 | $4.8 \times 10^3$ |
| | 6.6 | $2.1 \times 10^3$ |
| | 6.2 | $6.4 \times 10^2$ |
| | 5.1 | $4.0 \times 10^{2(t)}$ |
| F | 7.2 | $3.7 \times 10^3$ |
| | 6.8 | $2.0 \times 10^3$ |
| | 6.3 | $8.1 \times 10^2$ |
| | 5.4 | $1.4 \times 10^3$ |
| | 4.7 | $1.6 \times 10^3$ |
| | 4.5 | $1.6 \times 10^3$ |
| G | 7.2 | $3.0 \times 10^0$ |
| | 6.7 | $1.0 \times 10^1$ |
| | 5.9 | $1.0 \times 10^1$ |
| | 5.2 | $8.0 \times 10^0$ |
| | 4.5 | $8.0 \times 10^0$ |
| H | 7.5 | $2.0 \times 10^3$ |
| | 6.7 | $5.6 \times 10^2$ |
| | 6.3 | $2.8 \times 10^2$ |
| | 5.6 | $5.0 \times 10^2$ |
| | 4.8 | $6.3 \times 10^2$ |
| | 4.5 | $5.5 \times 10^2$ |
| | 3.7 | $6.9 \times 10^2$ |
| | 3.2 | $6.0 \times 10^2$ |
| J | 8.1 | $5.4 \times 10^4$ |
| | 7.1 | $2.6 \times 10^4$ |
| | 6.6 | $1.5 \times 10^4$ |
| | 5.2 | $8.0 \times 10^3$ |
| | 4.7 | $1.1 \times 10^4$ |
| | 4.0 | $1.2 \times 10^4$ |
| K | 7.0 | $4.8 \times 10^4$ |
| | 6.4 | $1.5 \times 10^4$ |
| | 5.9 | $1.0 \times 10^4$ |
| | 5.5 | $1.0 \times 10^4$ |
| | 4.8 | $1.4 \times 10^4$ |
| | 4.0 | $2.1 \times 10^4$ |
| | 2.4 | $1.6 \times 10^4$ |
| | 1.7 | $2.3 \times 10^4$ |
| | 1.2 | $1.8 \times 10^4$ |
| L | 7.2 | $3.0 \times 10^{3(t)}$ |
| | 7.0 | $3.1 \times 10^{3(t)}$ |
| | 6.9 | $2.8 \times 10^{3(t)}$ |
| | 6.1 | $4.4 \times 10^{3(t)}$ |
| | 4.5 | $7.5 \times 10^3$ |
| M | 7.4 | $1.1 \times 10^{3(t)}$ |
| | 7.1 | $1.1 \times 10^{3(t)}$ |
| | 6.8 | $1.2 \times 10^{3(t)}$ |
| | 6.4 | $1.3 \times 10^{3(t)}$ |
| | 4.7 | $2.5 \times 10^{3(t)}$ |
| N | 7.2 | $4.8 \times 10^{2(t)}$ |
| | 6.7 | $5.2 \times 10^{2(t)}$ |
| | 6.4 | $5.7 \times 10^{2(t)}$ |
| | 6.1 | $5.8 \times 10^{2(t)}$ |
| | 5.8 | $6.2 \times 10^{2(t)}$ |
| | 5.1 | $9.5 \times 10^2$ |
| O | 7.3 | $1.8 \times 10^{2(t)}$ |
| | 6.3 | $3.4 \times 10^{2(t)}$ |
| | 5.9 | $4.2 \times 10^{2(t)}$ |
| | 5.4 | $6.0 \times 10^{2(t)}$ |
| | 4.5 | $6.8 \times 10^{2(t)}$ |

$(t)$Turbid mixture.

It may readily be seen by a comparison of results, given in Table III, of Mixtures C, J, L and M, that the activated alkali-soluble emulsion thickeners produce significant thickening in acidified compositions, and that the preferred activated alkali-soluble emulsion thickeners produce thickening superior to that of other alkali-soluble emulsion thickeners; compare Mixture J with Mixtures L and M. It may further be seen that a wide variety of surfactants are operable in retaining the thickener activation upon acidification. By comparison of the results from Mixtures J and K, it may readily be seen that both weak, organic acids and strong, inorganic acids may be used as acidifying agents.

We claim:

1. A process for preparing a thickened, acidic, aqueous liquid which comprises the steps, performed in any order, of
    (a) mixing a thickening amount of an alkali soluble emulsion thickener or thickeners with an aqueous solution of from about 5% to about 40%, by weight based on the total weight of the liquid, of a surfactant selected from the group consisting of anionic, nonionic and amphoteric surfactants, and
    (b) neutralizing the thickener and the step, performed subsequent to the two above steps, of
    (c) acidifying the mixture.

2. The process of claim 1 wherein the thickener is neutralized to a pH above 6.5, and the mixture is acidified to a pH below 6.5.

3. The process of claim 2 wherein the mixture is acidified to a pH of from about 1.2 to about 6.5.

4. The process of claim 2 wherein the mixture is acidified to a pH of from about 3.5 to about 6.5.

5. The process of claim 1 wherein the mixture is acidified to a pH from about 5.0 to about 6.5.

6. The process of claim 1 wherein at least one of the thickeners comprises an aqueous dispersion of water-insoluble, emulsion copolymer obtained by aqueous emulsion copolymerization of (1) about 20% to about 50% by weight of methacrylic acid or acrylic acid, (2) about 0.5% to about 25% by weight of an acrylic or methacrylic acid ester of a $C_8$–$C_{30}$ alkyl, alkylaryl or polycyclic hydrocarbyl monoether of a polyethylene glycol having at least two oxyethylene units, this ester being defined by the following general formula:

$$H_2C=C(R)-C(O)-O-(CH_2CH_2O)_n-R°$$

wherein
R is H or $CH_3$,
n is from 2 to about 60, and
R° is a hydrophobic alkyl, alkylaryl, or polycyclic alkyl group having 8 to 30 carbon atoms, (3) about 40% to about 60% by weight of a $C_1$–$C_4$ alkyl acrylate or methacrylate, and (4) optionally, a small amount of a polyethylenically unsaturated monomer, the sum of the percentages of the copolymer components being 100%, and wherein the surfactant is compatible with the thickener or thickeners.

7. The process of claim 6 wherein component (1) is methacrylic acid, R of component (2) is $CH_3$—, n of component (2) is 20, R° of component (2) is mixed $C_{16}$ and $C_{18}$ alkyl, component 3 is ethyl acrylate, and component (4) is not present.

* * * * *